(12) United States Patent
Amid et al.

(10) Patent No.: US 6,610,006 B1
(45) Date of Patent: Aug. 26, 2003

(54) IMPLANTABLE PROSTHESIS

(75) Inventors: Parviz K. Amid, Calabasas, CA (US); Ronald L. Greene, Warwick, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/624,779

(22) Filed: Jul. 25, 2000

(51) Int. Cl.$^7$ .................................................. A61F 2/00
(52) U.S. Cl. .................... 600/37; 623/14.13; 623/23.72; 606/151
(58) Field of Search .................. 606/151, 213–215, 606/139; 623/1, 11.11, 23.72–23.76, 66.1, 14.13, 23.64–23.71; 600/37; 128/888, 897, 898

(56) References Cited

U.S. PATENT DOCUMENTS

| | | | |
|---|---|---|---|
| 2,671,444 A | 3/1954 | Pease, Jr. | |
| 3,988,411 A | 10/1976 | Capozza | |
| 4,345,414 A | 8/1982 | Bornat et al. | |
| 4,347,847 A | 9/1982 | Usher | |
| 4,403,604 A | 9/1983 | Wilkinson et al. | |
| 4,441,215 A | 4/1984 | Kaster | |
| 4,555,378 A | 11/1985 | Martin et al. | |
| 4,573,999 A | 3/1986 | Netto | |

(List continued on next page.)

FOREIGN PATENT DOCUMENTS

| | | |
|---|---|---|
| DE | 892 663 | 1/1953 |
| DE | 40 13 447 C1 | 2/1992 |
| EP | 0 265 157 A1 | 4/1988 |
| EP | 0 614 650 A2 | 9/1994 |
| EP | 0 836 838 A1 | 4/1998 |
| EP | 0 888 756 A2 | 1/1999 |
| EP | 0 898 944 A2 | 3/1999 |
| EP | 0 898 944 A3 | 8/1999 |
| FR | 2 682 284 A1 | 4/1993 |
| FR | 2 744 906 A1 | 8/1997 |
| FR | 2 769 825 A1 | 4/1999 |
| GB | 2 226 762 A | 7/1990 |
| WO | WO 92/13500 A1 | 8/1992 |
| WO | WO 95/07666 A1 | 3/1995 |

OTHER PUBLICATIONS

Amid, P.K., "Classification of biomaterials and their related complications in abdominal wall hernia surgery", Hernia, Mar. 25, 1997, pp. 15–21.

Amid, Parviz K., et al. "The Goal of Modern Hernia Surgery. How to Achieve Them: Open or Laparoscopic Repair?", Problems in General Surgery, 1995, pp. 165–171, vol. 12, Lippincott–Raven Publishers, Philadelphia.

*Primary Examiner*—David J. Isabella
*Assistant Examiner*—Urmi Chattopadhyay
(74) *Attorney, Agent, or Firm*—Wolf, Greenfield & Sacks, P.C.

(57) ABSTRACT

An implantable prosthesis for repairing an anatomical defect, such as a soft tissue and muscle wall defect. The prosthesis is configured to reduce the likelihood that an applied force at the repair site, such as due to intraabdominal pressure or tissue shrinkage, can lead to detrimental effects associated with tension at the anchoring locations between the prosthesis and host tissue and/or contraction of the prosthesis. In this regard, the prosthesis may be configured to limit the amount of tension at the anchoring locations caused by the application of a force or pressure to the prosthesis and/or contraction of the prosthesis. Alternatively, the prosthesis may be configured to compensate for contraction of the prosthesis due to tissue shrinkage at the repair site. The prosthesis may be configured to both limit tension at the anchoring locations and compensate for tissue shrinkage. The prosthesis may facilitate a reduction in postoperative discomfort, a recurrence of the defect, or the creation of a new defect associated with tension and/or prosthetic contraction.

89 Claims, 5 Drawing Sheets

U.S. PATENT DOCUMENTS

| | | |
|---|---|---|
| 4,693,720 A | 9/1987 | Scharnberg et al. |
| 4,728,328 A | 3/1988 | Hughes et al. |
| 4,769,038 A | 9/1988 | Bendavid et al. |
| 4,841,948 A | 6/1989 | Bauer et al. |
| 4,936,858 A | 6/1990 | O'Keeffe |
| 5,061,277 A | 10/1991 | Carpentier et al. |
| 5,116,357 A | 5/1992 | Eberbach |
| 5,146,933 A | 9/1992 | Boyd |
| 5,147,374 A | 9/1992 | Fernandez |
| 5,176,692 A | 1/1993 | Wilk et al. |
| 5,236,454 A | 8/1993 | Miller |
| 5,258,000 A | 11/1993 | Gianturco |
| 5,290,217 A | 3/1994 | Campos |
| 5,292,328 A | 3/1994 | Hain et al. |
| 5,306,296 A | 4/1994 | Wright et al. |
| 5,316,147 A | 5/1994 | Weber-Unger |
| 5,356,372 A | 10/1994 | Donovan et al. |
| 5,356,432 A | 10/1994 | Rutkow et al. |
| 5,368,602 A | 11/1994 | de la Torre |
| 5,379,754 A | 1/1995 | Tovey et al. |
| 5,383,477 A | 1/1995 | DeMatteis |
| 5,413,600 A | 5/1995 | Mittelman |
| 5,456,720 A | 10/1995 | Schultz et al. |
| 5,522,896 A | 6/1996 | Prescott |
| 5,578,045 A * | 11/1996 | Das .................... 604/159 |
| 5,584,884 A | 12/1996 | Pignataro |
| 5,593,441 A | 1/1997 | Lichtenstein et al. |
| 5,618,290 A * | 4/1997 | Toy et al. .................... 606/139 |
| 5,634,931 A | 6/1997 | Kugel |
| 5,674,279 A | 10/1997 | Wright et al. |
| 5,695,525 A | 12/1997 | Mulhauser et al. |
| 5,697,978 A | 12/1997 | Sgro |
| 5,713,842 A | 2/1998 | Kay |
| 5,716,408 A | 2/1998 | Eldridge et al. |
| 5,725,577 A | 3/1998 | Saxon |
| 5,743,917 A | 4/1998 | Saxon |
| 5,766,246 A | 6/1998 | Mulhauser et al. |
| 5,769,864 A | 6/1998 | Kugel |
| 5,824,082 A | 10/1998 | Brown |
| 5,916,225 A | 6/1999 | Kugel |
| 5,919,232 A | 7/1999 | Chaffringeon et al. |
| 5,954,767 A | 9/1999 | Pajotin et al. |
| D416,327 S | 11/1999 | Kugel |
| 5,990,378 A | 11/1999 | Ellis |
| 6,267,772 B1 * | 7/2001 | Mulhauser et al. ......... 606/151 |

* cited by examiner

IMPLANTABLE PROSTHESIS

FIELD OF THE INVENTION

The present invention relates to an implantable prosthesis and, more particularly, to a prosthesis for use in soft tissue repair and reconstruction.

DISCUSSION OF RELATED ART

Various prosthetic materials have been proposed to repair and reinforce anatomical defects, such as tissue and muscle wall hernias. For example, an inguinal hernia is commonly repaired using a sheet of biocompatible fabric, such as a knitted polypropylene mesh (BARD MESH). The fabric is typically sutured, stapled or otherwise provisionally anchored in place over, under or within the defect. Tissue integration with the fabric, such as by tissue ingrowth into and/or along the fabric, eventually completes the repair.

The attachment of the fabric to host tissue adjacent the defect can result in tension at the anchoring locations between the fabric and the tissue when abdominal pressure at the repair site is applied to the fabric, such as when an individual stands or strains, coughs, sneezes and the like. Tension at the anchoring locations may lead to postoperative pain for the patient, a recurrence of the defect, or the formation of a new defect. For example, a recurrence of the original defect or the creation of a new defect may result from failure of the suture line or other fastener, or tearing of the tissue due to tension at one or more of the anchoring locations. Tension on the suture line at the anchoring locations may also lead to ischemia of the tissue, resulting in enlargement of the suture holes and an eventual defect.

Scar formation (scarification) associated with the repair of tissue and wall defects may cause tissue shrinkage at the repair site, thereby contracting the repair fabric that has been integrated with tissue. Contraction of the fabric may cause patient discomfort as the fabric strains against the host tissue at the anchoring locations. Contraction of the fabric may cause failure of the fasteners and/or tearing of the tissue, in either case potentially leading to a recurrence of the defect, due to the fabric being pulled away from the tissue or muscle at the anchoring locations.

It is an object of the present invention to provide an improved method and a prosthesis for the repair of tissue or muscle wall defects.

SUMMARY OF THE INVENTION

The present invention is an implantable prosthesis and a method of repairing an anatomical defect, such as a tissue or muscle wall defect. The prosthesis is configured to reduce the likelihood that an applied force, such as due to intraabdominal pressure or tissue shrinkage, at the repair site can lead to detrimental effects associated with tension at the anchoring locations of the prosthesis and host tissue and/or contraction of the prosthesis. The prosthesis may reduce postoperative pain, and reduce the likelihood of either a recurrence of the defect or the creation of a new defect associated with tension and/or prosthetic contraction.

The prosthesis is particularly indicated for use in a repair in which tension and/or contraction are of potential concern. For techniques that employ fasteners, such as sutures, staples, adhesives and the like, to secure the prosthesis to the host tissue, the prosthesis may limit tension at the anchoring locations between the prosthesis and the host tissue. For fastener-less techniques, use of the prosthesis may be beneficial by limiting tension at the locations where tissue integrates with the prosthesis and/or by accommodating prosthetic contraction associated with shrinkage of tissue that has grown into and/or adhered to the prosthesis. The locations where fasteners join the prosthesis to host tissue and/or where tissue integrates with the prosthesis to secure the implant in place may all be referred to as "anchoring locations".

The prosthesis may include a patch formed of a biologically compatible, flexible implantable repair fabric suitable for reinforcing tissue and closing tissue or muscle wall defects. The repair fabric may include a body portion for covering at least a portion of the tissue or muscle wall defect and an anchoring portion for securing, with or without fasteners, the fabric to host tissue, including tissue, muscle or the like, adjacent the defect. The repair fabric may have a plurality of interstices that are constructed and arranged to allow tissue ingrowth. The prosthesis may also include a plug that is employed in combination with the patch and is configured to be placed within the defect.

In one embodiment of the invention, the repair fabric may include a preformed region configured to reduce the prospects that an applied force at the repair site will cause detrimental tension at the anchoring location and/or to compensate for contraction of the prosthesis that may occur as a result of tissue shrinkage at the repair site during scarification.

According to one aspect of the invention, the preformed region has a predetermined amount of laxity that is greater than an amount of laxity at an anchoring portion of the fabric to reduce the prospects that an applied force at the repair site will cause detrimental tension at the anchoring location. According to another aspect of the invention, the preformed region has a predetermined amount of compensation to compensate for contraction of the prosthesis. According to a further aspect of the invention, the preformed region is configured to both reduce detrimental tension at the anchoring portion and to compensate for prosthetic contraction.

In another embodiment of the invention, the implantable prosthesis may include a body portion having a preformed three-dimensional shape and a cavity with an open end that is configured to be disposed over the defect.

In a further embodiment of the invention, the implantable prosthesis may include a plurality of preformed indicia on the anchoring portion that correspond to predetermined anchoring locations between the prosthesis and the tissue or muscle.

The prosthesis is particularly suited for repairing a tissue or muscle wall hernia located in one or more of the inguinal region, the inguinofemoral region and the femoral region. The prosthesis may include a medial section and a lateral section that are configured to be positioned adjacent the medial corner and the lateral end of the inguinal canal, respectively, when the prosthesis is placed in the inguinal canal. The prosthesis may include an extension that is configured to extend into the femoral region and cover the femoral ring.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which.

DESCRIPTION OF ILLUSTRATIVE EMBODIMENTS

Figure 1:
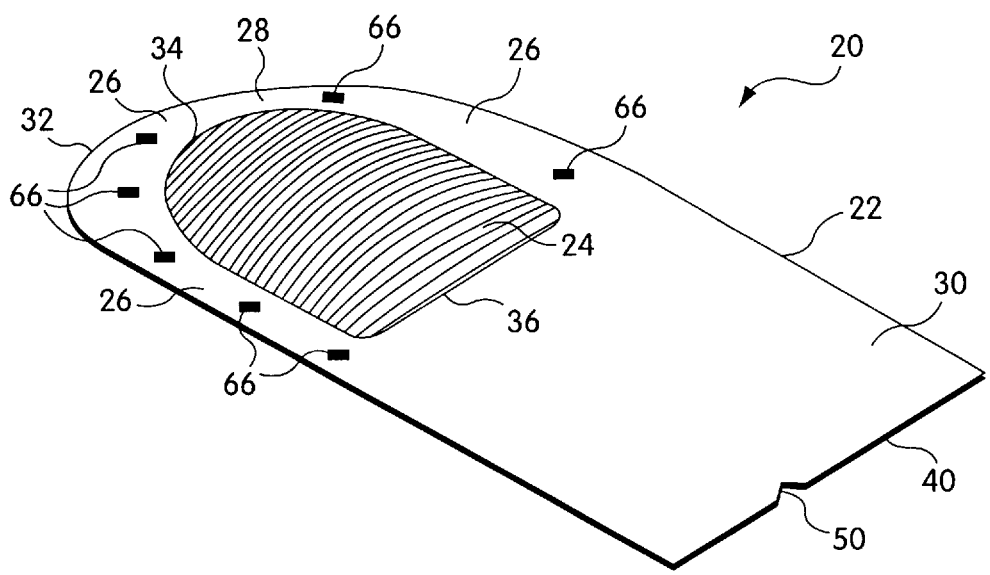
FIG. 1 is a top perspective view of an implantable prosthesis in accordance with one illustrative embodiment of the present invention.
Figure 2:
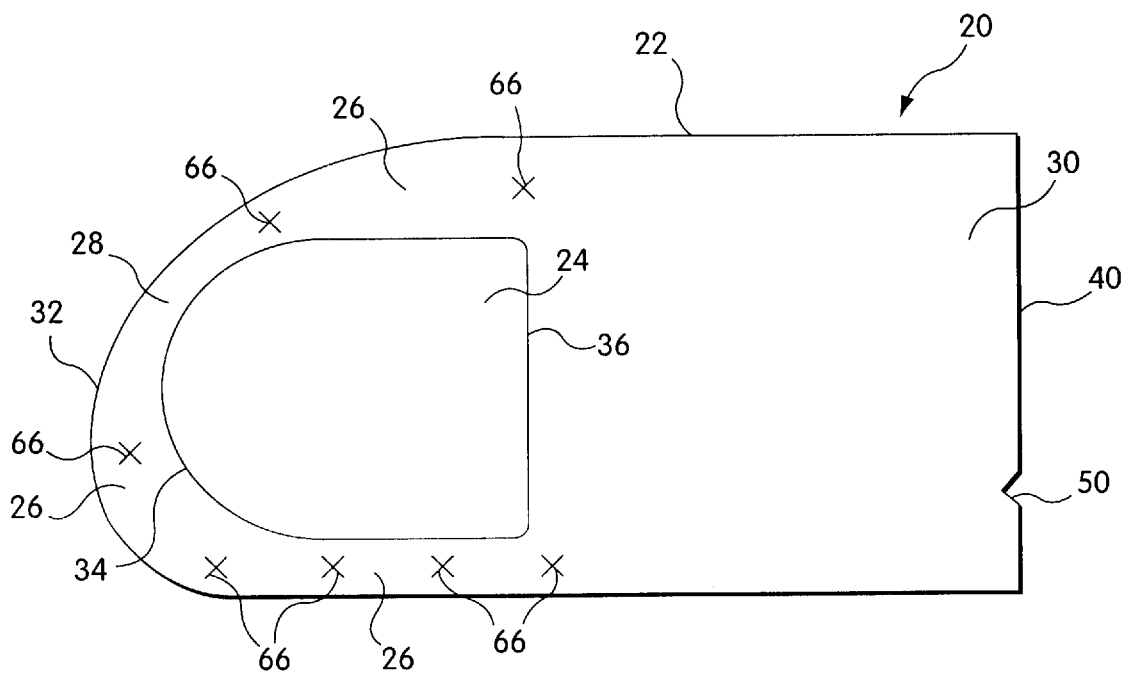
FIG. 2 is a top plan view of the implantable prosthesis of FIG. 1.
Figure 3:
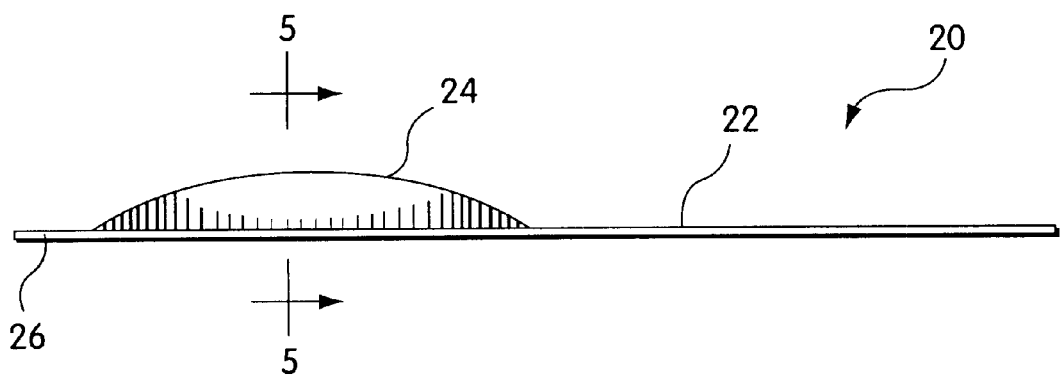
FIG. 3 is a side view of the implantable prosthesis of FIG. 1.
Figure 4:
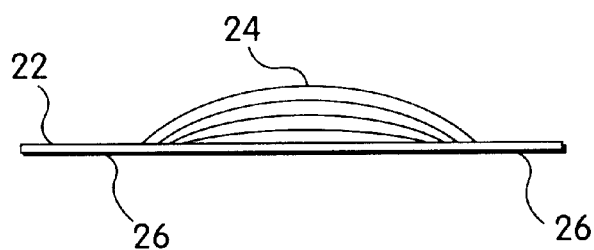
FIG. 4 is a front view of the implantable prosthesis of FIG. 1.
Figure 5:
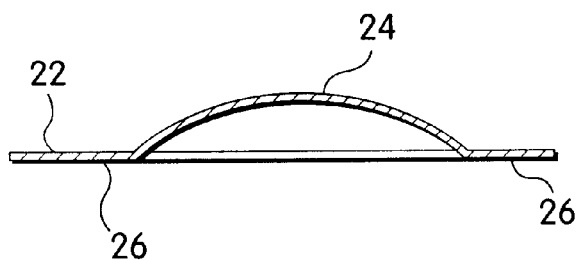
FIG. 5 is a cross-sectional view of the implantable prosthesis of FIG. 1 taken along section line 5—5 of FIG. 3.

FIGS. 1–5 illustrate one embodiment of an implantable prosthesis for repairing an anatomical defect, such as a soft tissue or muscle wall defect. The prosthesis is configured to reduce the likelihood that an applied force at the repair site, such as due to intraabdominal pressure or tissue shrinkage, can lead to detrimental effects associated with tension at the anchoring locations between the prosthesis and host tissue and/or contraction of the prosthesis. In this regard, the prosthesis may be configured to limit the amount of tension at the anchoring locations caused by the application of a force or pressure to the prosthesis and/or contraction of the prosthesis. Alternatively, the prosthesis may be configured to compensate for contraction of the prosthesis due to tissue shrinkage at the repair site. The prosthesis may be configured to both limit tension at the anchoring locations and compensate for tissue shrinkage. The prosthesis may facilitate a reduction in postoperative discomfort, a recurrence of the defect, or the creation of a new defect associated with tension and/or prosthetic contraction.

The prosthesis 20 includes a patch of prosthetic repair fabric 22 formed of a biologically compatible, flexible material. The patch 22 may include a body portion 24 for covering at least a portion of the tissue or muscle wall defect and an anchoring portion 26 for securing the fabric to host tissue, which may include tissue, muscle or the like, adjacent the defect. The patch may be combined with a plug of repair fabric that is configured to be placed within the defect.

In some repair techniques, a fastener, such as sutures, staples, adhesives and the like, may be employed to secure the anchoring portion 26 to the tissue or muscle. In a fastenerless repair technique, pressure, friction, tissue ingrowth and the like acting on the anchoring portion 26 may be used to secure the fabric to the tissue or muscle. The repair fabric may integrate with host tissue over time, and may include a plurality of interstices or openings which allow sufficient tissue ingrowth. The prosthetic fabric may, alternatively, be relatively non-porous, so as not to be susceptible to tissue infiltration.

Abdominal pressure or other forces applied at the repair site may lead to one or more of various detrimental effects associated with tension at the anchoring locations. Such detrimental effects may be alleviated by providing the implantable prosthesis with a preformed region having a predetermined amount of laxity that limits the amount of tension. In this regard, laxity refers to one or more of loose, slack, stretchable and like characteristics that accommodate forces at the repair site in a manner that limits tension.

In one illustrative embodiment, the body portion 24 is configured with a region of laxity. As shown, the body portion 24 may have a preformed three-dimensional shape, such as a dome, that is configured to overlie and cover the defect. The body portion may be configured to be larger than the defect so that the body portion extends across and covers the entire defect. One or more anchoring portions 26 extend from the body portion 24 for securing the fabric to the tissue or muscle adjacent the defect at one or more anchoring locations. The anchoring portions 26 may be disposed partially or completely about the body portion 24, and may be planar, as illustrated, or configured to the shape of the anchoring locations at the repair site. Further, the anchoring portions may be conformable to the anatomy of interest.

The dome is configured to provide an amount of laxity that is greater than the laxity of the anchoring portion. The dome includes a surface that is placed over and in spaced relation to the defect when the prosthesis is implanted in the repair site. The dome has an open end that may be disposed over and exposed to the defect so that the defective tissue or muscle may extend into the dome, such as due to intraabdominal pressure, without exerting an excessive amount of force on the prosthesis that may lead to detrimental tension. In this regard, the dome may be configured to allow the defective tissue or muscle to fill the dome cavity and contact the dome surface with less force than were the body portion not initially spaced from the defect. This arrangement accommodates an increase in pressure or other forces in the repair region with minimal, if any, tension being applied to the tissue or muscle at the anchoring locations.

As illustrated, the dome may be configured with a generally spherical or curved shape. It is to be appreciated, however, that the dome may be configured to have any shape that is suitable to receive the tissue or muscle therein.

Although illustrated as part of the body portion 24, it is contemplated that the region of laxity may be provided on any portion of the repair fabric 22 that is suitable to limit tension at the anchoring locations between the prosthesis and tissue. For example, and without limitation, the region of laxity also may be located in the anchoring portion 26, or between the body portion 24 and the anchoring portion. The region of laxity may also be comprised of two or more regions located in various portions of the patch 22 to provide laxity in selected regions of the prosthesis.

It is also to be appreciated that the region of laxity may be formed in any manner suitable to reduce the detrimental effects of tension at the anchoring locations. For example, the region may employ a pleated or other configuration that allows the region to expand under an applied force or pressure so as to alleviate or limit tension between the fabric and the tissue or muscle at the anchoring locations. The region may also employ a material having different size filaments and/or a knit or weave pattern that allows the region to expand or otherwise absorb an increase in pressure in the repair region. The region of laxity may be formed with a material that is different than the material forming other portions of the prosthesis.

When tissue integration with a prosthesis occurs during the repair process, tissue shrinkage at the repair site may lead to one or more of various detrimental effects associated with contraction of the prosthesis. Such detrimental effects may be alleviated by providing the implantable prosthesis with a preformed region of compensation that compensates for the tissue shrinkage by accommodating an anticipated amount of fabric contraction in the repair region.

In one illustrative embodiment, the body portion 24 includes a region of compensation that provides additional material to compensate for fabric contraction that may occur due to tissue shrinkage, so that the body portion continues to cover the defect after scarification. This arrangement may reduce the incidence of a recurrence to the extent that the prosthesis does not tend to pull away and separate from the tissue or muscle to which it is secured when the integrated tissue shrinks.

The amount of contraction generally depends on the extent of tissue integration with the prosthesis. For example, as the amount of tissue integration increases, the amount of fabric contraction also tends to increase. In this regard, the pore size of the fabric may influence the amount of tissue integration, and therefore the amount of prosthetic contraction. As the pore size increases, the fabric may experience a greater amount of tissue growth into the pores, which may lead to a larger amount of fabric contraction during tissue shrinkage.

In the embodiment shown in FIGS. 1–5, the body portion 24 may have a preformed three-dimensional shape, such as a dome, which is configured to overlie the defect and to provide an additional amount of material, as compared to a flat body portion, that compensates for fabric contraction. During tissue shrinkage, the dome contracts to alleviate detrimental effects on the prosthesis. In one embodiment, the dome is configured with an amount of fabric that is capable of accommodating a range of fabric contraction from approximately 15% to approximately 25%. It is to be appreciated, however, that the particular amount of material provided by the dome may be adjusted to accommodate any anticipated amount of contraction.

It is contemplated that the region of compensation may be provided on any portion of the patch 22 that is suitable to compensate for contraction of the prosthesis. For example, the region of compensation may be located adjacent the body portion 24. The region of compensation may also be comprised of two or more regions located in various portions of the patch to provide compensation for fabric contraction in selected regions of the prosthesis.

It is also to be appreciated that the region of compensation may be formed in any manner suitable to accommodate prosthetic contraction. For example, similar to the region of laxity described above, the region of compensation may employ a pleated or other configuration that provides sufficient material to allow the region to accommodate fabric contraction so as to alleviate patient discomfort or separation of the fabric from the tissue or muscle. In this regard, the pleats may be configured to allow fabric expansion due to increased pressure or other forces applied at the repair region which, if retained, may compensate for prosthetic contraction The region of compensation may also employ a material having different size filaments and/or a knit or weave pattern that allows the region to accommodate tissue shrinkage during scarification. The region of compensation may be formed from a material that is different than the material forming other portions of the prosthesis.

As one of ordinary skill would readily appreciate, the prosthesis may be configured both to relieve tension at the anchoring locations, associated with pressure or other variables at the repair site, and to accommodate fabric contraction associated with tissue shrinkage at the repair region. In the embodiment illustrated in FIGS. 1–5, the body portion 24 is configured to include the region of laxity and the region of compensation. It is to be understood, however, that the prosthesis 20 may include a region of laxity that is separate from the region of compensation. Further, the region of laxity may have a construction that differs from the region of compensation in terms of one or more of shape, size, material and the like.

The prosthesis 20 may be particularly suited to the repair of inguinal hernias. In the illustrative embodiment shown in FIGS. 1–5, the patch 22 includes a medial section 28 and a lateral section 30 that are configured to be positioned adjacent the medial corner and the lateral end of the inguinal canal, respectively. The medial section 28 of the prosthesis may include a generally rounded medial edge 32 that is configured to extend beyond the medial corner of the inguinal canal for anchoring the prosthesis. The body portion 24 may be configured with a rounded medial segment 34. As illustrated, the medial segment 34 may be spaced inwardly from the medial edge 32 of the prosthesis to provide the patch with an anchoring portion 26 between the medial edge 32 and the medial segment 34. It is to be appreciated, however, that the medial segment 34 of the body portion may extend to the peripheral edge, including the medial edge 32, of the patch. The body portion may also include a lateral segment 36 that is located proximate to the center of the prosthesis so that it is positioned adjacent the internal ring. As shown, the body portion may have a generally D-shaped periphery, although any shape may be employed to suit a particular prosthetic application.

Figure 6:
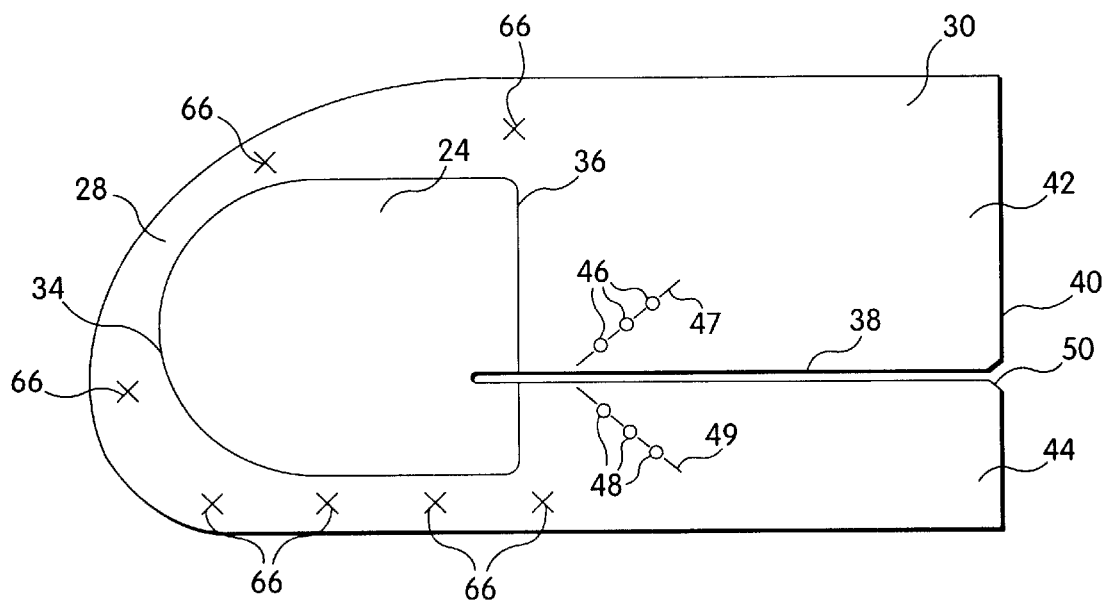
FIG. 6 is a top plan view of an implantable prosthesis in accordance with another illustrative embodiment of the present invention.

As illustrated in an embodiment shown in FIG. 6, the prosthesis 20 may have a slit 38 extending inwardly from the lateral edge 40 of the patch to create a pair of tails 42, 44 that are separated to receive the spermatic cord proximate the lateral segment 36 of the body portion. The tails 42, 44 may be crossed around the cord and stitched or otherwise secured to each other to reinforce the internal ring. To aid a surgeon in this regard, it may be desirable to provide the prosthesis with a locking feature that may be employed to secure the tails to each other.

In one embodiment, the locking feature includes one or more pairs of fasteners 46, 48 that are disposed on the tails 42, 44 and configured to mate with each other in a male/female-type arrangement when the tails are crossed about the cord. As shown in FIG. 6, a series of fasteners 46, 48 may be located along a portion of the length and on opposite sides of the slit 38. The fasteners 46, 48 may extend along nonparallel lines 47, 49 that are angled relative to the slit 38 so that the fasteners become aligned with each other when the tails are crossed about the cord. The fasteners may include snaps, zipper-type strips, and like arrangements that may be integrally preformed in the fabric. In another embodiment, the locking feature may include a suture that is attached to one of the tails and is to be passed through at least the opposite tail to secure the tails together when they are crossed about the cord. Of course, it is to be understood that any suitable locking feature apparent to one of skill in the art may be employed to secure the tails about the cord.

The slit 38 may be preformed with the prosthesis 20 or formed by the surgeon during the repair procedure. To facilitate formation of the slit 38, the prosthesis may include an indicator that is configured to identify the location and/or length of the slit. In one embodiment, the patch includes a notch 50 along the lateral edge 40 that identifies a preferred location for the slit. It is to be appreciated, however, that any suitable indicator may be employed to aid the surgeon in locating and forming the slit. For example, the indicator may include a series of holes, contrasting color stitches and the like that run along a portion of the prosthesis and correspond to the location, length and/or orientation of the slit. The indicator may be marked on the prosthesis using a suitable ink or dye.

In some instances, a surgeon may find it desirable to repair or reinforce the femoral region by itself or in conjunction with an inguinal hernia repair. It is, therefore, contemplated that the prosthesis 20 may be configured to reinforce the inguinofemoral region or femoral region of an individual.

Figure 7:
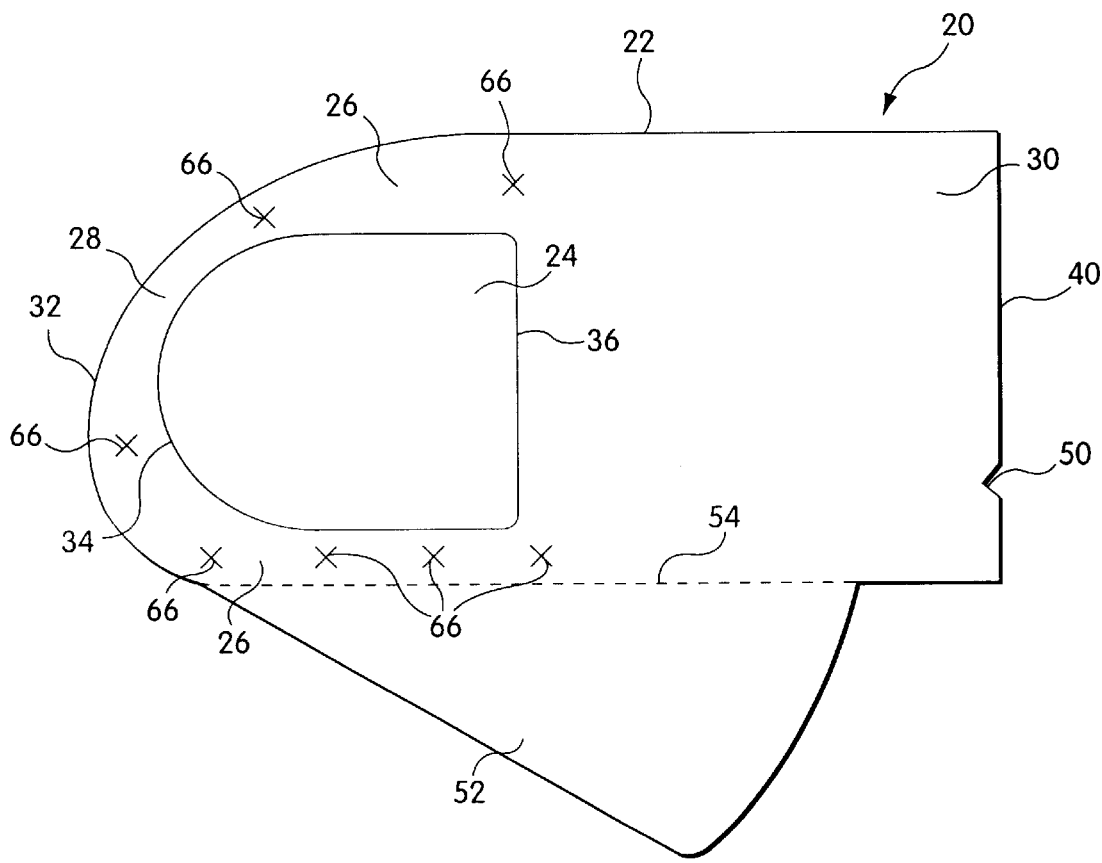
FIG. 7 is a top plan view of an implantable prosthesis in accordance with a further illustrative embodiment of the present invention.

In one illustrative embodiment shown in FIG. 7, the prosthesis 20 includes an extension 52 that is configured to extend downwardly into the space of Retzius to Cooper's ligament and cover the femoral ring upon implantation. As shown, the extension 52 may be configured with a triangular shape that conforms generally to the femoral region. It is to be appreciated, however, that the prosthesis may employ an extension having any desirable shape. The extension is foldable along a fold line 54 so that it may be oriented approximately 90° relative to the remainder of the prosthesis to accommodate the configuration of the inguinofemoral region when implanted. It is contemplated that the prosthesis may be preformed with the extension 52 oriented at a desired angle to facilitate implantation of the prosthesis in the inguinofemoral region.

In the illustrative embodiment, the extension 52 is integrally formed with the prosthesis from a single sheet of fabric. Alternatively, the extension may be formed as a separate piece of the prosthesis that is attached to the patch 22. It is to be appreciated, however, that the prosthesis 20 may be formed in any suitable manner.

Figure 8:
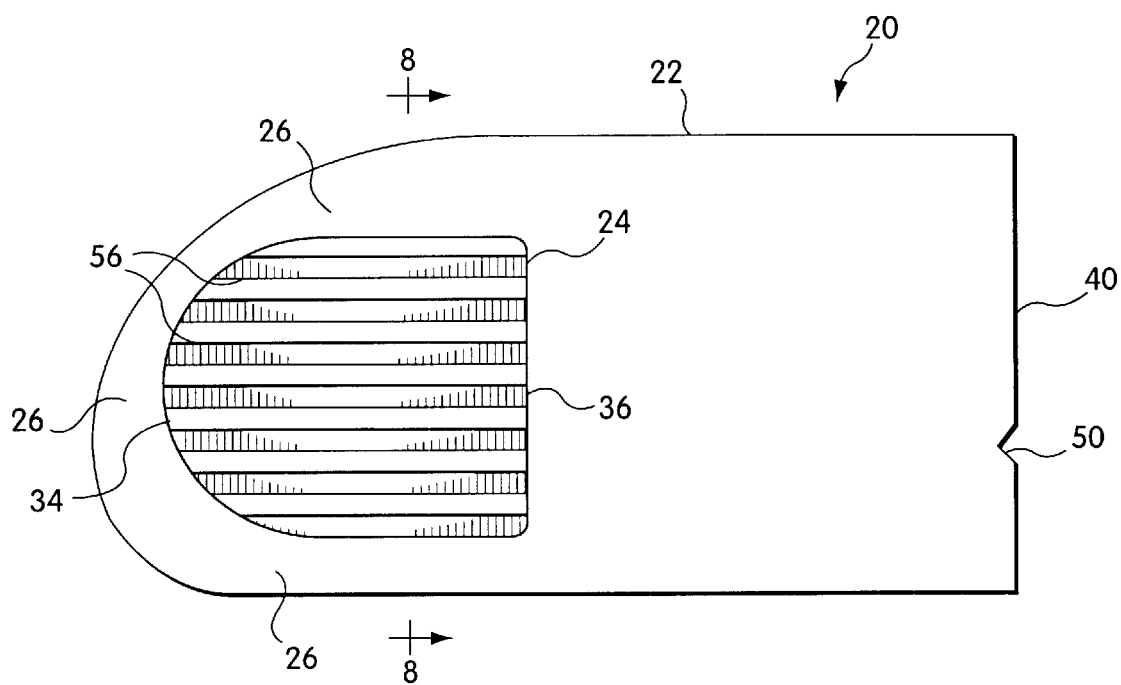
FIG. 8 is a top plan view of an implantable prosthesis in accordance with another illustrative embodiment of the present invention.
Figure 9:
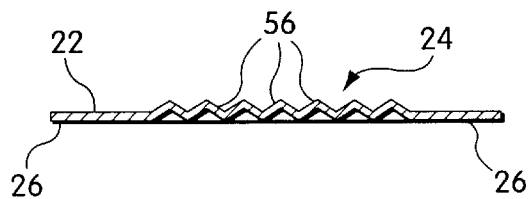
FIG. 9 is a cross-sectional view of the implantable prosthesis of FIG. 8 taken along section line 9—9 of FIG. 8 and rotated counter-clockwise.
Figure 10:
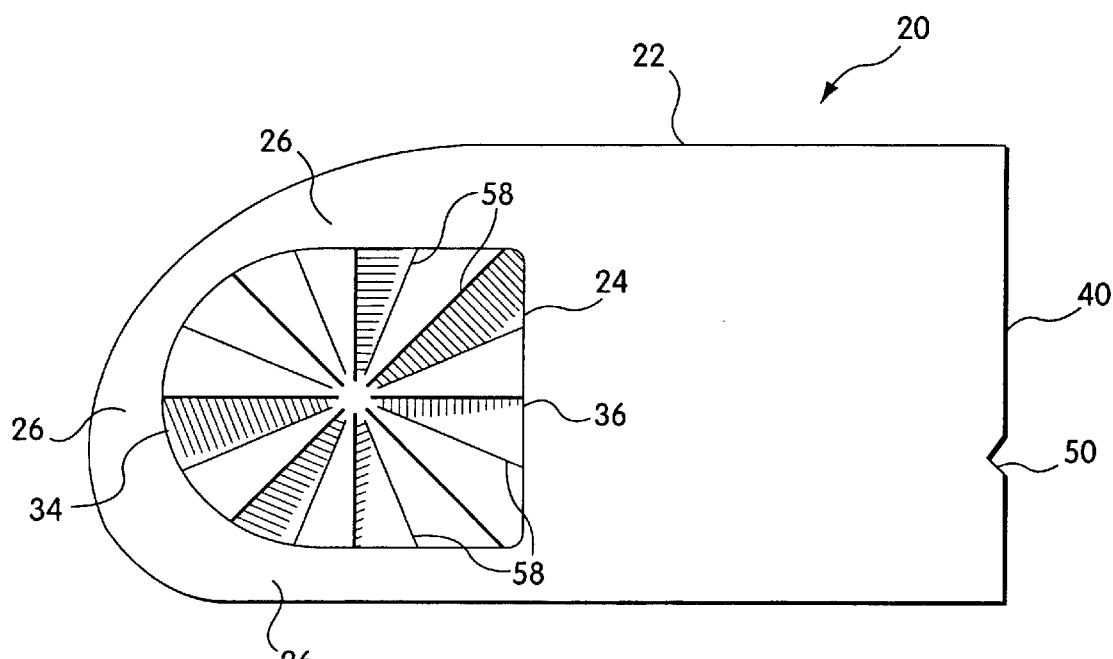
FIG. 10 is a top plan view of an implantable prosthesis in accordance with a further illustrative embodiment of the present invention.

As indicated above, the prosthesis may include a region of laxity and/or a region of compensation that employ any configuration suitable to provide a desired amount of laxity and compensation, respectively. FIGS. 8–10 illustrate various other embodiments for a prosthesis that includes a region of laxity and/or a region of compensation. It is to be appreciated that these embodiments are exemplary and other suitable prosthetic configurations may be implemented for such repairs.

FIGS. 8–9 illustrate an embodiment of a prosthesis 20 that includes a body portion 24 preformed with a plurality of pleats 56 to provide a region of laxity. As illustrated, the pleats 56 may be arranged in an accordion-like fashion to provide additional material across the width of the patch 22 that are configured to expand to accommodate increased pressure or other forces applied at the repair region. When expanded, the additional material provided by the pleats may also compensate for tissue shrinkage at the repair region.

FIG. 10 illustrates another embodiment of a prosthesis that includes a body portion 24 preformed with a plurality of pleats 58 that are arranged in an umbrella-like, radial fashion. This arrangement of pleats 58 may also provide a region of laxity and a region of compensation.

It is to be appreciated that the various body portion configurations illustrated in FIGS. 1–10 are not intended to be exhaustive.

The body portion 24 may be integrally formed with the anchoring portion 26 from a single sheet of fabric. The body portion 24 may be molded or otherwise preformed in the fabric to have any shape and size suitable for providing a desired amount of laxity and/or compensation. It is to be appreciated, however, that the prosthesis 20 may be formed in any suitable manner.

It is contemplated that the body portion 24 may be preformed as a separate piece of the prosthesis that is attached to the patch fabric. A prosthesis formed in this manner may facilitate the use of various shapes, materials and the like for the body portion.

Figure 11:
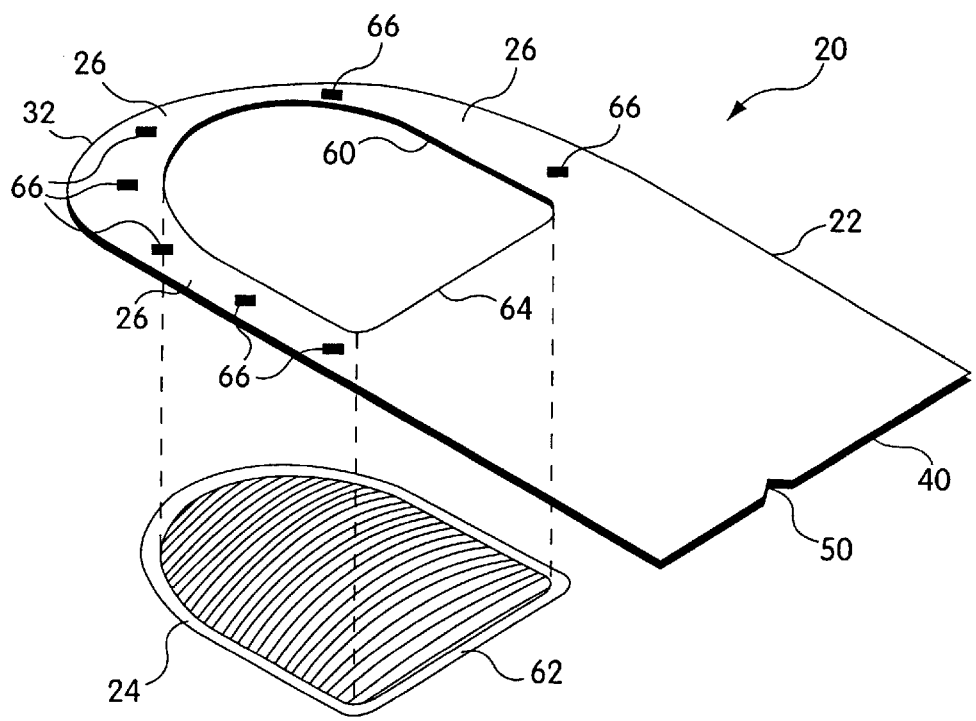
FIG. 11 is an exploded perspective view of an implantable prosthesis in accordance with another illustrative embodiment of the present invention.

In one illustrative embodiment shown in FIG. 11, a preformed body portion 24 is positioned in a hole 60 in a piece of fabric with the outer periphery 62 of the body portion 24 being attached to the inner periphery 64 of the hole 60 employing any suitable fastening technique. For example, the preformed body portion 24 may be stitched or bonded to the fabric using stitches or an adhesive dispensed about the periphery of the body portion. Alternatively, the body portion 24 may be laminated or heat fused to the fabric by a combination of heat and pressure. The junction between the body portion and the fabric may also be configured to enhance the laxity and/or compensation characteristics of the prosthesis by being more elastic than one or both of the body portion 24 and the remaining patch fabric.

In some instances, it may be desirable to provide one or more indicia on the prosthesis that aid a surgeon in attaching the prosthesis at preferred anchoring locations, such as by suturing, stapling and the like, to the tissue or muscle adjacent the defect. In one illustrative shown in FIGS. 1–5, a plurality of preformed indicia 66 are provided on the anchoring portion 26 about several sides of the body portion 24. The indicia 66 include a monofilament thread of contrasting color relative to the repair fabric to indicate the desired anchoring location. The number and location of the indicia 66 may be chosen based on the particular type of repair and/or surgical technique being employed to make the repair. It is to be appreciated that any suitable indicia 66 may be provided on the prosthesis. For example, the indicia may include bumps, dimples, holes and the like, or may be marked on the prosthesis with a contrasting color ink or dye.

In one embodiment, the prosthesis 20 is formed of a sheet of knitted polypropylene monofilament mesh fabric such as BARD MESH available from C. R. Bard, Inc. When implanted, the polypropylene mesh promotes rapid tissue ingrowth into and around the mesh structure. Alternatively, other surgical materials which are suitable for tissue reinforcement and defect closure may be utilized including PROLENE, SOFT TISSUE PATCH (microporous ePTFE), SURGIPRO, TRELEX, ATRIUM and MERSELENE. Absorbable materials, including polyglactin (VICRYL), polyglycolic acid (DEXON) and collagen, may be suitable for applications involving temporary repair of tissue or wall defects. It also is contemplated that the mesh fabric may be formed from multifilament yarns and that any suitable method, such as weaving, molding and the like, may be employed to form the prosthetic mesh material.

In some instances, it may be desirable to employ a repair fabric that does not promote tissue ingrowth. For such an application, the repair fabric may be formed from a sheet of expanded polytetrafluoroethylene (ePTFE), such as PRECLUDE Pericardial Membrane, PRECLUDE Peritoneal Membrane and PRECLUDE Dura Substitute membrane available from W. L. Gore & Associates, Inc., having a pore size (submicronal) that discourages tissue ingrowth. A representative and non-limiting sampling of other suitable non-porous materials includes silicone elastomer, such as SILASTIC Rx Medical Grade Sheeting (Platinum Cured) distributed by Dow Corning Corporation, TEFLON mesh, and microporous polypropylene sheeting (CELGARD) and film.

It is to be appreciated that any suitable materials may be used for the repair fabric as would be apparent to one of skill in the art.

In an exemplary embodiment particularly suited for the repair of an inguinal hernia, the patch 22 includes an approximately 0.025 to 0.030 inch thick sheet of BARD MESH knitted from polypropylene monofilament with a diameter of approximately 0.006 inches. The patch 22 has a length along the longitudinal axis of approximately 5.97 inches and a width between the side edges of approximately 2.36 inches. The body portion 24 includes a dome having a height of approximately 0.256 inches. In another embodiment, the dome height may be approximately 0.334 inches. The body portion 24 has a length of approximately 2.36 inches and a width of approximately 1.86 inches. The medial segment 34 of the body portion has a radius of approximately 0.93 inches. These dimensions represent a prosthesis that may be trimmed as necessary by a surgeon to conform to the particular size and shape of the inguinal canal. It should be understood, however, that these dimensions are merely exemplary and that any suitable sizes and shapes may be employed for the prosthesis.

In one embodiment, the body portion 24 is formed in the sheet of mesh fabric using a die having male and female components that are configured with the desired shape for the dome. The fabric is sandwiched between the die components and exposed to a temperature of approximately 270° F. for approximately 2 hours. It is to be appreciated, however, that any suitable manufacturing process may be employed to fabricate the prosthesis.

The present invention provides an implantable prosthesis that may have one or more of the following advantages. The prosthesis 20 may reduce the likelihood that an applied force and/or tissue shrinkage at the repair site can lead to detrimental effects associated with either tension at the anchoring locations between the prosthesis and host tissue, contraction of the prosthesis, or both tension and contraction. The prosthesis may also reduce postoperative pain associated with tension and/or contraction that could interfere with the individual's ability to undertake daily activities and/or lengthen the recovery period from the repair of a defect. The prosthesis may be sutured, stapled and the like to the tissue or muscle and/or anchored in place by tissue integration.

The prosthesis 20 may be pliable to allow a surgeon to manipulate the shape of the implant to conform to the anatomical site of interest and to be secured thereto. The shape and size of the implant may vary according to the surgical application as would be apparent to one of skill in the art. In this regard, it is contemplated that the patch 22 may be preshaped or, instead, selectively shaped by the surgeon during the surgical procedure.

The prosthesis 20 of the present invention is particularly indicated for repair of inguinal hernias. One representative repair technique includes the Lichtenstein "tension-free" repair technique in which a piece of flat mesh fabric is sutured in the inguinal canal to cover and reinforce the hernia in a manner that limits tension at the anchoring locations between the mesh and the surrounding tissue. The prosthesis 20 of the present invention facilitates this technique by providing the surgeon with a repair fabric that includes a preformed region of laxity and/or compensation that enhances the surgeon's ability to achieve a tension-free repair.

It should be understood that the foregoing description of the invention is intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect, the implantable prosthesis comprising:
a patch of prosthetic repair fabric including a body portion that is constructed and arranged to cover at least a portion of the tissue or muscle wall defect and an anchoring portion that is constructed and arranged to secure the patch to host tissue or muscle, the patch further including a preformed region that is constructed and arranged to reduce the incidence of the detrimental effect of tension at the anchoring portion when the patch is secured to the tissue or muscle and a force is applied at the tissue or muscle wall defect and/or to compensate for contraction of the patch relative to the tissue or muscle, wall defect due to tissue shrinkage during scarification, the preformed region having a three-dimensional shape and including a preformed dome having an open end that is configured to be disposed over the tissue or muscle wall defect.

2. The implantable prosthesis according to claim 1, wherein the anchoring portion is substantially planar.

3. The implantable prosthesis according to claim 1, wherein the body portion includes the preformed region.

4. The implantable prosthesis according to claim 3, wherein the body portion has a three-dimensional shape.

5. The implantable prosthesis according to claim 1, wherein the preformed region is formed from a material that is different from the anchoring portion.

6. The implantable prosthesis according to claim 1, wherein the prosthetic repair fabric has a plurality of interstices that are constructed and arranged to allow tissue ingrowth.

7. The implantable prosthesis according to claim 1, wherein the patch is constructed and arranged to repair an inguinal hernia.

8. The implantable prosthesis according to claim 7, wherein the patch includes a medial edge that is configured to extend beyond the medial corner of the inguinal canal.

9. The implantable prosthesis according to claim 8, wherein the body portion includes a rounded medial segment spaced inwardly from the medial edge of the patch.

10. The implantable prosthesis according to claim 7, wherein the patch includes an extension that extends from the body portion and is configured to cover the femoral ring of an individual.

11. The implantable prosthesis according to claim 10, wherein the extension has a triangular shape.

12. The implantable prosthesis according to claim 10, wherein the extension is constructed and arranged to be oriented at an angle relative to the body portion.

13. The implantable prosthesis according to claim 1, wherein the patch includes a plurality of indicia that correspond to desired anchoring locations for the implantable prosthesis, the plurality of indicia being preformed on the anchoring portion.

14. The implantable prosthesis according to claim 13, wherein the plurality of indicia include a monofilament thread having a contrasting color relative to the prosthetic repair fabric.

15. The implantable prosthesis according to claim 1, wherein the preformed region is constructed and arranged to reduce the incidence of detrimental tension at the anchoring portion, the preformed region having a predetermined amount of laxity that is greater than an amount of laxity at the anchoring portion.

16. The implantable prosthesis according to claim 1, wherein the preformed region is constructed and arranged to compensate for contraction of the patch relative to the tissue or muscle wall defect.

17. The implantable prosthesis according to claim 1, wherein the preformed region is constructed and arranged to reduce the incidence of detrimental tension at the anchoring portion and to compensate for contraction of the patch relative to the tissue or muscle wall defect.

18. The implantable prosthesis according to claim 1, further comprising a plug that is coupled to the patch, the plug configured to be placed within the tissue or muscle wall defect.

19. The implantable prosthesis according to claim 1, wherein the body portion and the anchoring portion are integrally formed from a sheet of repair fabric.

20. An implantable prosthesis for repairing a tissue or muscle wall defect, the implantable prosthesis comprising:
a patch of prosthetic repair fabric including a body portion that is constructed and arranged to cover at least a portion of the tissue or muscle wall defect and an anchoring portion that is constructed and arranged to secure the patch to host tissue or muscle, the patch further including a preformed region that is constructed and arranged to reduce the incidence of the detrimental effect of tension at the anchoring portion when the patch is secured to the tissue or muscle and a force is applied at the tissue or muscle wall defect and/or to compensate for contraction of the patch relative to the tissue or muscle wall defect due to tissue shrinkage during scarification, the preformed region having a three-dimensional shape and the anchoring portion being substantially planar, the body portion and the anchoring portion being integrally formed from a sheet of repair fabric.

21. The implantable prosthesis according to claim 20, wherein the body portion includes the preformed region.

22. The implantable prosthesis according to claim 20, wherein the prosthetic repair fabric has a plurality of interstices that are constructed and arranged to allow tissue ingrowth.

23. The implantable prosthesis according to claim 20, wherein the patch is constructed and arranged to repair an inguinal hernia.

24. The implantable prosthesis according to claim 23, wherein the patch includes a medial edge that is configured to extend beyond the medial corner of the inguinal canal.

25. The implantable prosthesis according to claim 24, wherein the body portion includes a rounded medial segment spaced inwardly from the medial edge of the patch.

26. The implantable prosthesis according to claim 23, wherein the patch includes an extension that extends from the body portion and is configured to cover the femoral ring of an individual.

27. The implantable prosthesis according to claim 26, wherein the extension has a triangular shape and is constructed and arranged to be oriented at an angle relative to the body portion.

28. The implantable prosthesis according to claim 20, wherein the preformed region is constructed and arranged to reduce the incidence of detrimental tension at the anchoring portion.

29. The implantable prosthesis according to claim 20, wherein the preformed region is constructed and arranged to compensate for contraction of the patch relative to the tissue or muscle wall defect.

30. An implantable prosthesis for repairing a tissue or muscle wall defect, the implantable prosthesis comprising:
a patch of prosthetic repair fabric including a body portion that is constructed and arranged to cover at least a portion of the tissue or muscle wall defect and an anchoring portion that is constructed and arranged to secure the patch to host tissue or muscle, the patch further including a preformed region that is constructed and arranged to reduce the incidence of the detrimental effect of tension at the anchoring portion when the patch is secured to the tissue or muscle and a force is applied at the tissue or muscle wall defect and/or to compensate for contraction of the patch relative to the tissue or muscle wall defect due to tissue shrinkage during scarification, the body portion having a three-dimensional shape and including the preformed region, wherein the body portion include a preformed dome having an open end that is configured to be disposed over the tissue or muscle wall defect.

31. The implantable prosthesis according to claim 20, wherein the anchoring portion is substantially planar.

32. An implantable prosthesis for repairing a tissue or muscle wall defect, the implantable prosthesis comprising:
a patch of an implantable layer of mesh fabric including a body portion having a preformed three-dimensional shape that is constructed and arranged to cover at least a portion of the tissue or muscle wall defect and an anchoring portion extending from the body portion that is constructed and arranged to secure the implantable prosthesis to host tissue or muscle, the body portion having a cavity with an open end that is configured to be disposed over the tissue or muscle wall defect.

33. The implantable prosthesis according to claim 32, wherein the body portion has a dome defining the cavity.

34. The implantable prosthesis according to claim 32, wherein the anchoring portion is substantially planar.

35. The implantable prosthesis according to claim 34, wherein the body portion and the anchoring portion are integrally formed from a sheet of mesh fabric.

36. The implantable prosthesis according to claim 32, wherein the mesh fabric has a plurality of interstices that are constructed and arranged to allow tissue ingrowth.

37. The implantable prosthesis according to claim 32, wherein the patch is constructed and arranged to repair an inguinal hernia.

38. The implantable prosthesis according to claim 37, wherein the patch includes a medial edge that is configured to extend beyond the medial corner of the inguinal canal.

39. The implantable prosthesis according to claim 38, wherein the body portion includes a rounded medial segment spaced inwardly from the medial edge of the patch.

40. The implantable prosthesis according to claim 34, wherein the medial edge of the patch is rounded.

41. The implantable prosthesis according to claim 37, wherein the patch includes an extension that extends from the body portion and is configured to cover the femoral ring of an individual.

42. The implantable prosthesis according to claim 41, wherein the extension has a triangular shape.

43. The implantable prosthesis according to claim 41, wherein the extension is constructed and arranged to be oriented at an angle relative to the body portion.

44. The implantable prosthesis according to claim 32, wherein the patch includes a plurality of indicia that correspond to desired anchoring locations for the implantable prosthesis, the plurality of indicia being preformed on the anchoring portion.

45. The implantable prosthesis according to claim 44, wherein the plurality of indicia include a monofilament thread having a contrasting color relative to the mesh fabric.

46. The implantable prosthesis according to claim 32, wherein the patch has a substantially planar shape.

47. An implantable prosthesis for repairing a tissue or muscle wall defect, the implantable prosthesis comprising:
   a prosthetic repair fabric including a body portion that is constructed and arranged to overlie at least a portion of the tissue or muscle wall defect and an anchoring portion that is constructed and arranged to secure the prosthetic repair fabric to tissue or muscle adjacent the tissue or muscle wall defect, the prosthetic repair fabric including a plurality of preformed indicia on the anchoring portion that correspond to desired anchoring locations between the implantable prosthesis and the tissue or muscle, the body portion having a three-dimensional shape and including a preformed dome having an open end that is configured to be disposed over the tissue or muscle wall defect.

48. The implantable prosthesis according to claim 47, wherein the anchoring portion is substantially planar.

49. The implantable prosthesis according to claim 44, wherein the body portion and the anchoring portion are integrally formed from a sheet of repair fabric.

50. The implantable prosthesis according to claim 49, wherein the prosthetic repair fabric is constructed and arranged to repair an inguinal hernia in the inguinal canal.

51. The implantable prosthesis according to claim 49, wherein the body portion has a three-dimensional shape.

52. The implantable prosthesis according to claim 49, where the anchoring portion is substantially planar.

53. The implantable prosthesis according to claim 47, wherein the prosthetic repair fabric has a plurality of interstices that are constructed and arranged to allow tissue ingrowth.

54. The implantable prosthesis according to claim 47, wherein the prosthetic repair fabric is constructed and arranged to repair an inguinal hernia in the inguinal canal.

55. The implantable prosthesis according to claim 54, wherein the prosthetic repair fabric includes a medial edge that is configured to extend beyond the medial corner of the inguinal canal.

56. The implantable prosthesis according to claim 55, wherein the body portion includes a rounded medial segment spaced inwardly from the medial edge of the prosthetic repair fabric.

57. The implantable prosthesis according to claim 54, wherein the prosthetic repair fabric includes an extension that extends from the body portion and is configured to cover the femoral ring of an individual.

58. The implantable prosthesis according to claim 57, wherein the extension has a triangular shape.

59. The implantable prosthesis according to claim 58, wherein the extension is constructed and arranged to be oriented at an angle relative to the body portion.

60. The implantable prosthesis according to claim 47, wherein the plurality of indicia include a monofilament thread having a contrasting color relative to the prosthetic repair fabric.

61. The implantable prosthesis according to claim 47, wherein the plurality of indicia correspond to the anchoring locations associated with a tension-free inguinal hernia repair technique.

62. An implantable prosthesis for repairing a tissue or muscle wall defect in the inguinal canal, the implantable prosthesis comprising:
   a patch of prosthetic repair fabric configured to be implanted in the inguinal canal, the patch having a rounded medial edge that is configured to extend beyond the medial corner of the inguinal canal, the patch including
      a body portion that is constructed and arranged to cover at least a portion of the tissue or muscle wall defect, the body portion including a rounded medial segment that is spaced inwardly from the medial edge of the patch, the body portion projecting outwardly from the patch, to define a cavity having an open end that is configured to be disposed over the tissue or muscle wall defect; and
      a substantially planar anchoring portion extending from the body portion that is constructed and arranged to secure the patch to host tissue or muscle,
      the body portion being constructed and arranged to reduce the incidence of detrimental tension at the anchoring portion when the patch is secured to the tissue or muscle and a force is applied at the tissue or muscle wall defect and/or to compensate for contraction of the patch relative to the tissue or muscle wall defect due to tissue shrinkage during scarification.

63. The implantable prosthesis according to claim 62, wherein the patch includes a plurality of preformed indicia on the anchoring portion that correspond to desired anchoring locations between the implantable prosthesis and the host tissue or muscle.

64. A method of repairing a tissue or muscle wall defect, the method comprising steps of:
   (a) providing an implantable prosthesis including a patch having a body portion for covering the tissue or muscle wall defect and an anchoring portion for securing the implantable prosthesis to host tissue or muscle, the implantable prosthesis being preformed with a region that is constructed and arranged to reduce the incidence of detrimental tension at the anchoring portion when the patch is secured to the tissue or muscle and a force is applied at the tissue or muscle wall defect and/or to compensate for contraction of the patch relative to the tissue or muscle wall defect to reduce the incidence of detrimental effects due to tissue shrinkage during scarification, the preformed region including a three-dimensional shape and a dome having an open end; and
   (b) implanting the implantable prosthesis with the body portion covering at least a portion of the tissue or muscle wall defect.

65. The method according to claim 64, wherein the anchoring portion is substantially planar.

66. The method according to claim 64, wherein step (b) includes implanting the implantable prosthesis in an inguinal canal to repair an inguinal hernia.

67. The method according to claim 66, wherein the implantable prosthesis includes a medial edge that extends beyond the medial corner of the inguinal canal.

68. The method according to claim 67, wherein the body portion includes a rounded medial segment that is spaced inwardly from the medial edge of the implantable prosthesis.

69. The method according to claim 66, wherein step (b) includes implanting the implantable prosthesis to repair or reinforce the femoral region of an individual.

70. The method according to claim 69, wherein the implantable prosthesis includes an extension that extends from the body portion and is configured to cover the femoral ring.

71. The method according to claim 70, wherein the extension has a triangular shape.

72. The method according to claim 70, wherein the extension is oriented at an angle relative to the body portion.

73. The method according to claim 64, wherein the implantable prosthesis includes a plurality of indicia on the anchoring portion that correspond to desired anchoring locations for the implantable prosthesis.

74. The method according to claim 64, wherein the preformed region is constructed and arranged to reduce the incidence of detrimental tension at the anchoring portion, the preformed region having a predetermined amount of laxity that is greater than an amount of laxity at the anchoring portion.

75. The method according to claim 64, wherein the preformed region is constructed and arranged to compensate for contraction of the patch relative to the tissue or muscle wall defect.

76. The method according to claim 64, wherein the preformed region is constructed and arranged to reduce the incidence of detrimental tension at the anchoring portion and to compensate for contraction of the patch relative to the tissue or muscle wall defect.

77. A method of repairing a tissue or muscle wall defect, the method comprising steps of:
 (a) providing an implantable prosthesis including a body portion preformed with a three-dimensional shape that is configured to cover at least a portion of the tissue or muscle wall defect and an anchoring portion extending from the body portion that is constructed and arranged to secure the implantable prosthesis to host tissue or muscle, the body portion having a cavity with an open end that is configured to be disposed over the tissue or muscle wall defect; and
 (b) implanting the implantable prosthesis with the cavity covering at least a portion of the tissue or muscle wall defect.

78. The method according to claim 77, wherein the body portion includes a dome.

79. The method according to claim 78, wherein the anchoring portion is substantially planar.

80. The method according to claim 77, wherein step (b) includes implanting the implantable prosthesis in an inguinal canal to repair an inguinal hernia.

81. The method according to claim 80, wherein the implantable prosthesis includes a medial edge that extends beyond the medial corner of the inguinal canal.

82. The method according to claim 81, wherein the body portion includes a rounded medial segment that is spaced inwardly from the medial edge of the implantable prosthesis.

83. The method according to claim 80, wherein step (b) includes implanting the implantable prosthesis to repair or reinforce the femoral region of an individual.

84. The method according to claim 83, wherein the implantable prosthesis includes an extension that extends from the body portion and is configured to cover the femoral ring.

85. The implantable prosthesis according to claim 84, wherein the extension has a triangular shape.

86. The implantable prosthesis according to claim 84, wherein the extension is oriented at an angle relative to the body portion.

87. The method according to claim 77, wherein the implantable prosthesis includes a plurality of indicia on the anchoring portion that correspond to desired anchoring locations for the implantable prosthesis.

88. The method according to claim 77, wherein the implantable prosthesis includes a plurality of interstices that are constructed and arranged to allow tissue ingrowth.

89. An implantable prosthesis for repairing a tissue or muscle wall defect in the inguinal region, the implantable inguinal region prosthesis comprising:
 a flexible patch of prosthetic repair fabric having openings constructed and arranged for tissue ingrowth, said patch being elongated in a medial to lateral direction and including a roughly D-shaped medial portion,
 said medial portion including a pre-formed dome that projects outwardly from the patch, said dome defining a cavity for covering at least a portion of the tissue or muscle wall defect.

* * * * *

UNITED STATES PATENT AND TRADEMARK OFFICE
CERTIFICATE OF CORRECTION

PATENT NO. : 6,610,006 B1
DATED : August 26, 2003
INVENTOR(S) : Parviz K. Amid and Ronald L. Green It is certified that error appears in the above-identified patent and that said Letters Patent is hereby corrected as shown below:

Column 10,
Line 26, replace "muscle, wall" with -- muscle wall --.

Column 12,
Line 21, replace "include" with -- includes --.
Line 24, replace "20" with -- 30 --.

Column 13,
Line 26, replace "44" with -- 47 --.

Column 14,
Line 14, replace "patch, to" with -- patch to --.

Signed and Sealed this

Twenty-seventh Day of January, 2004

JON W. DUDAS
*Acting Director of the United States Patent and Trademark Office*